(12) United States Patent
Nadin et al.

(10) Patent No.: US 7,655,675 B2
(45) Date of Patent: *Feb. 2, 2010

(54) GAMMA-SECRETASE INHIBITORS

(75) Inventors: Alan John Nadin, Sawbridgeworth (GB); Andrew Pate Owens, Huntingdon (GB); Martin Richard Teall, Bishops Stortford (GB)

(73) Assignee: Merck Sharp & Dohme Limited, Hoddeson (GB)

( * ) Notice: Subject to any disclaimer, the term of this patent is extended or adjusted under 35 U.S.C. 154(b) by 785 days.

This patent is subject to a terminal disclaimer.

(21) Appl. No.: 10/957,251

(22) Filed: Oct. 1, 2004

(65) Prior Publication Data

US 2005/0075320 A1   Apr. 7, 2005

(30) Foreign Application Priority Data

Oct. 4, 2003   (GB)   ................... 0323258.4

(51) Int. Cl.
*A61K 31/40* (2006.01)
*A61K 31/44* (2006.01)
*C07D 207/48* (2006.01)
*C07D 211/96* (2006.01)

(52) U.S. Cl. .................. 514/317; 514/424; 546/194; 548/542

(58) Field of Classification Search ................. 546/194
See application file for complete search history.

(56) References Cited

U.S. PATENT DOCUMENTS 6,890,956 B2 * 5/2005 Churcher et al. ............ 514/602

FOREIGN PATENT DOCUMENTS

| WO | WO 00/50391   | 8/2000  |
| WO | WO 01/70677   | 9/2001  |
| WO | WO 02/081435  | 10/2002 |
| WO | WO 03/018543  | 3/2003  |
| WO | WO 2004/031139 | * 4/2004 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online],[retrieved on Sep. 23, 2003].Retrieved from the Internet, URL; http://www.cnn.com/2003/HEALTH/conditions/09/24/alzheimers.drug.ap/indexhtml>.*

* cited by examiner

*Primary Examiner*—Rebecca L Anderson
*Assistant Examiner*—Shawquia Young
(74) *Attorney, Agent, or Firm*—William Krovatin; Raynard Yuro

(57) ABSTRACT

Compounds of formula I:

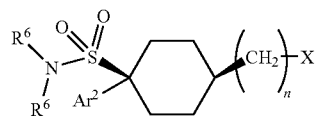

inhibit the processing of APP by gamma-secretase and hence find use in treatment of Alzheimer's disease.

2 Claims, No Drawings

GAMMA-SECRETASE INHIBITORS

The present invention relates to a novel class of compounds, their salts, pharmaceutical compositions comprising them, processes for making them and their use in therapy of the human body. In particular, the invention relates to novel cyclohexyl sulphonamides which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are various reports in the literature of compounds with inhibitory activity towards γ-secretase, as measured in cell-based assays. These are reviewed in WO 01/70677. Many of the relevant compounds are peptides or peptide derivatives.

WO 00/50391 discloses a broad class of sulphonamides as modulators of the production of β-amyloid, but neither discloses nor suggests the compounds of the present invention.

WO 02/081435 and WO 03/018543 disclose cyclohexyl sulphones having activity against γ-secretase, but neither disclose nor suggest the compounds of the present invention.

The present invention provides a novel class of cyclohexyl sulphonamides which are useful in the treatment or prevention of AD by inhibiting the processing of APP by γ-secretase, thus arresting the production of Aβ.

According to the invention, there is provided a compound of formula I:

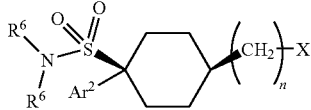

wherein n is 0, 1, 2 or 3;

X represents H, halogen, CN, $N_3$, OH, $OR^1$, $N(R^2)_2$, $CO_2H$, $CO_2R^1$, $OCOR^1$, CHO, $COR^1$, $CON(R^2)_2$, $OCON(R^2)_2$, SCN, $SR^1$, $S(O)R^1$, $SO_2R^1$, $SO_2N(R^2)_2$, $OSO_2N(R^2)_2$, $NHCOR^1$, $NHCO_2R^1$, $NHCON(R^2)_2$, $NHSO_2R^1$ or $NHSO_2N(R^2)_2$;

$R^1$ represents $CF_3$ or $C_{1-6}$alkyl, $C_{2-6}$alkenyl, $C_{3-9}$cycloalkyl or $C_{3-6}$cycloalkyl$C_{1-6}$alkyl, any of which may bear up to 2 substituents selected from halogen, CN, $CF_3$, $OR^3$, aryloxy, $COR^3$, $CO_2R^3$, $OCOR^4$, $SO_2R^4$, $N(R^5)_2$, and $CON(R^5)_2$, or $R^1$ represents aryl, aryl$C_{1-6}$alkyl, C-heterocyclyl or C-heterocyclyl$C_{1-6}$alkyl;

each $R^2$ independently represents H or $C_{1-6}$alkyl, $C_{2-6}$alkenyl, $C_{3-9}$cycloalkyl or $C_{3-6}$cycloalkyl$C_{1-6}$alkyl, any of which may bear up to 2 substituents selected from halogen, CN, $CF_3$, $OR^3$, $COR^3$, $CO_2R^3$, $OCOR^4$, $SO_2R^4$ and $CON(R^5)_2$;

or two $R^2$ groups together with a nitrogen atom to which they are mutually attached complete an N-heterocyclyl group;

$R^3$ represents H or $C_{1-4}$alkyl;

$R^4$ represents $C_{1-4}$alkyl;

$R^5$ represents H or $C_{1-4}$alkyl, or two $R^5$ groups together with a nitrogen atom to which they are mutually attached complete an azetidine, pyrrolidine, piperidine, morpholine, thiomorpholine or thiomorpholine-1,1-dioxide ring;

each $R^6$ independently represents H, $C_{1-6}$alkyl, $C_{3-6}$cycloalkyl or $C_{2-6}$alkenyl, any of which is optionally substituted with up to 3 halogen atoms or with CN; or the two $R^6$ groups and the nitrogen to which they are attached complete an N-heterocyclyl group or a heteroaryl group which is attached through N;

$Ar^2$ represents phenyl or heteroaryl, either of which bears 0-3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

"aryl" at every occurrence thereof refers to phenyl or heteroaryl which optionally bear up to 3 substituents selected from halogen, CN, $NO_2$, $CF_3$, $OCF_3$, OH, $COR^3$, $CO_2R^3$, $OCOR^4$, $N(R^5)_2$, $CON(R^5)_2$ and optionally-substituted $C_{1-6}$alkyl, $C_{1-6}$alkoxy, $C_{2-6}$alkenyl or $C_{2-6}$alkenyloxy wherein the substituent is selected from halogen, CN, $CF_3$, phenyl, $OR^3$, $CO_2R^3$, $OCOR^{3a}$, $N(R^5)_2$ and $CON(R^5)_2$; and "C-heterocyclyl" and "N-heterocyclyl" at every occurrence thereof refer respectively to a heterocyclic ring system attached through carbon or nitrogen, said ring system being non-aromatic and comprising up to 10 atoms, at least one of which is O, N or S, and optionally bearing up to 3 substituents selected from oxo, halogen, CN, $NO_2$, $CF_3$, $OCF_3$, $OR^3$, $COR^3$, $CO_2R^3$, $OCOR^4$, $OSO_2R^4$, $N(R^5)_2$, $CON(R^5)_2$ and optionally-substituted phenyl, $C_{1-6}$alkyl, $C_{1-6}$alkoxy, $C_{2-6}$alkenyl or $C_{2-6}$alkenyloxy wherein the substituent is selected from halogen, CN, $CF_3$, $OR^3$, $CO_2R^3$, $OCOR^4$, $N(R^5)_2$ and $CON(R^5)_2$;

or a pharmaceutically acceptable salt thereof.

Where a variable occurs more than once in formula I, the individual occurrences are independent of each other, unless otherwise indicated.

As used herein, the expression "$C_{1-x}$ alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "$C_{3-9}$cycloalkyl" as used herein refers to nonaromatic monocyclic or fused bicyclic hydrocarbon ring systems comprising from 3 to 9 ring atoms. Examples include cyclopropyl, cyclobutyl, cyclopentyl, cyclohexyl, cyclohexenyl and bicyclo[2.2.1]heptyl. Monocyclic systems of 3 to 6 members are preferred.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "heterocyclyl" as defined herein includes both monocyclic and fused bicyclic systems of up to 10 ring atoms selected from C, N, O and S. Mono- or bicyclic systems of up to 7 ring atoms are preferred, and monocyclic systems of 4, 5 or 6 ring atoms are most preferred. Examples of heterocyclic ring systems include azetidinyl, pyrrolidinyl, 3-pyrrolinyl, terahydrofuryl, 1,3-dioxolanyl, tetrahydrothiophenyl, tetrahydropyridinyl, piperidinyl, piperazinyl, morpholinyl, thiomorpholinyl, imidazolidinyl, oxazolidinyl, thiazolidinyl, 2,5-diazabicyclo[2.2.1]heptyl, 2-aza-5-oxabicyclo[2.2.1]heptyl and 1,4-dioxa-8-azaspiro[4.5]decanyl. Unless otherwise indicated, heterocyclyl groups may be attached through a ring carbon atom or a ring nitrogen atom where present. "C-heterocyclyl" indicates attachment through carbon, while "N-heterocyclyl" indicates attachment through nitrogen.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Monocyclic systems of 5 or 6 members are preferred. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine. Pyridine rings may be in the N-oxide form. Heteroaryl groups are typically attached through carbon, but where the heteroaryl group comprises a 5-membered ring consisting of carbon and nitrogen atoms, attachment may alternatively be via nitrogen.

Where a phenyl group or heteroaryl group bears more than one substituent, preferably not more than one of said substituents is other than halogen or alkyl.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, benzenesulphonic acid, methanesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula I, n is 0, 1, 2 or 3, preferably 0, 1 or 2, most preferably 0 or 1.

X represents H, halogen, CN, $N_3$, OH, $OR^1$, $N(R^2)_2$, $CO_2H$, $CO_2R^1$, $OCOR^1$, CHO, $COR^1$, $CON(R^2)_2$, $OCON(R^2)_2$, SCN, $SR^1$, $S(O)R^1$, $SO_2R^1$, $SO_2N(R^2)_2$, $OSO_2N(R^2)_2$, $NHCOR^1$, $NHCO_2R^1$, $NHCON(R^2)_2$, $NHSO_2R^1$ or $NHSO_2N(R^2)_2$. Preferred identities of X include CN, $N_3$, OH, $CO_2H$, $CO_2R^1$, $CON(R^2)_2$, $SO_2R^1$, $SO_2N(R^2)_2$, $OSO_2N(R_2)_2$, $NHCOR^1$, $NHCO_2R^1$, $NHCON(R_2)_2$, $NHSO_2R^1$ or $NHSO_2N(R^2)_2$.

In one subset of the compounds of formula I, n is 1 or 2 and X represents CN, $N_3$, OH, $CO_2H$, $CO_2R^1$, $CON(R^2)_2$, $SO_2R^1$, $SO_2N(R^2)_2$ or $OSO_2N(R^2)_2$. Within this subset, X preferably represents $CO_2H$, $CO_2R^1$, $CON(R^2)_2$, $SO_2R^1$ or $SO_2N(R^2)_2$.

In a second subset of the compounds of formula I, n is 0 and X represents $NHCOR^1$, $NHCO_2R^1$, $NHCON(R^2)_2$, $NHSO_2R^1$ or $NHSO_2N(R^2)_2$. Within this embodiment, X preferably represents $NHSO_2R^1$ or $NHSO_2N(R^2)_2$, most preferably $NHSO_2R^1$.

$R^1$ is preferably $CF_3$, aryl or arylalkyl, or an alkyl, cycloalkyl or cycloalkylalkyl group, optionally substituted as described previously. Preferred substituents include halogen (especially fluorine or chlorine), $CF_3$, CN, $OR^3$ (especially OH, OMe and OEt), $COR^3$ (especially acetyl), $CO_2R^3$ (especially $CO_2H$, $CO_2Me$ and $CO_2Et$) and $CON(R^5)_2$ (especially $CONH_2$).

Examples of alkyl groups represented by $R^1$ include methyl, ethyl, n-propyl, isopropyl, t-butyl, isobutyl, 2,2,2-trifluoroethyl, cyanomethyl, 2-hydroxyethyl, 2-methoxyethyl, 2-hydroxy-2-methylpropyl, carboxymethyl, ethoxycarbonylmethyl, 1-carboxyethyl, 1-ethoxycarbonylethyl, carbamoylmethyl and $MeCOCH_2$—.

Examples of cycloalkyl and cycloalkylalkyl groups represented by $R^1$ include cyclopropyl, cyclobutyl, cyclopentyl, cyclohexyl, cyclopropylmethyl and cyclopentylmethyl.

When $R^1$ represents aryl or arylalkyl, the aryl group may be phenyl or heteroaryl, optionally substituted as defined previously. Preferred substituents include halogen (especially chlorine or fluorine), $CF_3$, $OCF_3$, alkyl (especially methyl), OH and alkoxy (especially methoxy). Preferred heteroaryl groups include pyridine, pyrimidine, furan, thiophene, thiazole, imidazole, triazole, thiadiazole and tetrazole.

Examples of aryl groups represented by $R^1$ include phenyl, 2-fluorophenyl, 4-fluorophenyl, 2,4-difluorophenyl, 2-chlorophenyl, 2-, 3- and 4-hydroxyphenyl, 2-trifluoromethoxyphenyl, 2-methoxyphenyl, 2-pyridyl (and the corresponding N-oxide), 4-pyridyl, 2-pyrimidinyl, 2-furyl, 2-thienyl, 2-thiazolyl, 2-imidazolyl, 2-methylfuran-3-yl, 4-methylthiazol-3-yl, 5-methyl-1,3,4-thiadiazol-2-yl, 1-methylimidazol-2-yl, 1-methyl-1,2,3,4-tetrazol-5-yl, 1,2,4-triazol-3-yl, 1-methyl-1,2,4-triazol-3-yl, 2-methyl-1,2,4-triazol-3-yl and 4-methyl-1,2,4-triazol-3-yl.

Arylalkyl groups represented by $R^1$ are typically optionally substituted benzyl, phenethyl, heteroarylmethyl or heteroarylethyl groups. Examples include benzyl, 2-furylmethyl, 2-thienylmethyl and 1-(2-thienyl)ethyl.

When X represents $S(O)R^1$, $R^1$ very aptly represents aryl, for example 2-pyridyl or 1-methyl-1,2,3,4-tetrazol-5-yl.

When X represents $NHCO_2R^1$, $R^1$ very aptly represents $C_{1-6}$alkyl (for example methyl) or arylalkyl (for example benzyl).

When X represents $NHCOR^1$, $R^1$ very aptly represents $C_{1-6}$alkyl (for example methyl) or substituted $C_{1-6}$alkyl (for example 2,2,2-trifluoroethyl or 1-hydroxy-2,2,2-trifluoroethyl).

For any $N(R^2)_2$ fragment, preferably either at least one of the $R^2$ groups represents H or $C_{1-6}$alkyl such as methyl, or the two $R^2$ groups complete an N-heterocyclyl group.

When $N(R^2)_2$ does not represent N-heterocyclyl, preferably one $R^2$ is H or methyl and the other is H or optionally substituted alkyl or cycloalkyl. Preferred substituents include $CF_3$, $OR^3$ (such as OH and OMe), $CO_2R^3$ (such as t-butoxycarbonyl) and $OCOR^4$ (such as acetoxy). Within this embodiment, preferred identities for $N(R^2)_2$ include $NH_2$, NHMe, NHEt, $NH^iPr$, $NH^tBu$, $NMe_2$, NH-cyclobutyl, $NHCH_2CF_3$, $NHCH_2CO_2{}^tBu$, $NHCH_2CH_2OCOMe$ and $NHCH_2CH_2OH$.

When $N(R^2)_2$ represents N-heterocyclyl, the heterocyclic ring is typically an optionally substituted azetidine, pyrrolidine, 3-pyrroline, piperidine, morpholine, thiomorpholine or 2-aza-5-oxabicyclo[2.2.1]heptane ring. Azetidine and pyrrolidine are preferred, and azetidine is particularly preferred. Preferred substituents include oxo, halogen (especially fluorine), $CF_3$, $OR^3$ (especially OH), $OCOR^4$ (especially acetoxy and trimethylacetoxy), $OSO_2R^4$ (especially methanesulphonyloxy), $CO_2R^3$ (especially $CO_2H$ and $CO_2Me$), $N(R^5)_2$ (especially dimethylamino) and alkyl (especially methyl). Examples of preferred N-heterocyclyl groups include azetidin-1-yl, pyrrolidin-1-yl, 3-pyrrolin-1-yl, piperidin-1-yl, morpholin-4-yl, thiomorphonlin-4-yl, 2-aza-5-oxabicyclo[2.2.1]hept-2-yl, 3-oxo-azetidin-1-yl, 3-hydroxyazetidin-1-yl, 3acetoxyazetidin-1-yl, 3-(dimethylamino)azetidin-1-yl, 3-methanesulphonyloxyazetidin-1-yl, 3,3-difluoroazetidin-1-yl, 3-hydroxy-3-methylazetidin-1-yl, 2-carboxypyrrolidin-1-yl, 2-methoxycarbonylpyrrolidin-1-yl, 3-fluoropyrrolidin-1-yl, 3,3-difluoropyrrolidin-1-yl, 2-(trifluoromethyl)pyrrolidin-1-yl, 3-oxo-pyrrolidin-1-yl, 3-hydroxypyrrolidin-1-yl, 3-hydroxy-3-methylpyrrolidin-1-yl, 3-(trimethylacetoxy)pyrrolidin-1-yl, 4-(trifluoromethyl)piperidin-1-yl and 4,4-difluoropiperidin-1-yl.

When X represents $NHCON(R^2)_2$, very aptly both $R^2$ groups represent methyl, or one $R^2$ represents H and the other represents $C_{1-6}$alkyl, such as methyl or ethyl.

The two $R^6$ groups independently represent H, $C_{1-6}$alkyl, $C_{3-6}$cycloalkyl or $C_{2-6}$alkenyl, any of which is optionally substituted with up to 3 halogen atoms or with CN; or the two $R^6$ groups and the nitrogen to which they are attached complete an N-heterocyclyl group or a heteroaryl group which is attached through N. Preferably, the two $R^6$ groups do not both represent H. Examples of alkyl groups represented by $R^6$ include methyl, ethyl, n-propyl, n-butyl. 3-methylbutyl, 3,3,3-trifluoropropyl and 4,4,4-trifluorobutyl. Examples of alkenyl groups represented by $R^6$ include allyl, but-2-enyl and 3-methylbut-2-enyl.

When the two $R^6$ groups complete an N-heterocyclyl group, said heterocyclic group typically comprises 4, 5, 6 or 7 ring atoms, preferably 5 or 6 ring atoms, and is optionally substituted as defined previously. Preferred rings include pyrrolidine, 3-pyrroline and piperidine. Preferred substituents include $C_{1-6}$alkyl (such as methyl), halogen (such as fluorine) and $CF_3$. Alternatively, the two $R^6$ groups may complete an N-heteroaryl group such as pyrrol-1-yl, imidazol-1-yl, triazol-1-yl, tetrazol-1-yl or indol-1-yl, of which pyrrol-1-yl is preferred. Preferred examples of cyclic groups represented by $N(R^6)_2$ include 4-fluoropiperidin-1-yl, 4,4-difluoropiperidin-1-yl, 4-(trifluoromethyl)piperidin-1-yl, pyrrolidin-1-yl, 3-pyrrolin-1-yl and pyrrol-1-yl, of which 4,4-difluoropiperidin-1-yl and 4-(trifluoromethyl)piperidin-1-yl are particularly preferred.

$Ar^2$ preferably represents optionally substituted phenyl, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5-positions or in the 2-, 3- and 6-positions, or from phenyl groups bearing a fluorine substituent in the 2-position and halogen, CN, methyl or hydroxymethyl in the 5-position. In a preferred embodiment of the invention, $Ar^2$ represents 2,5-difluorophenyl.

Examples of compounds in accordance with the invention include compounds of formula I in which $Ar^2$ represents 2,5-difluorophenyl and the other variables are as indicated in the following table:

| n | X | $N(R^6)_2$ |
|---|---|---|
| 0 | $NHSO_2CF_3$ | 4,4-di-F-piperidin-1-yl |
| 0 | $NHSO_2CF_3$ | 4-$CF_3$-piperidin-1-yl |
| 0 | $NHSO_2CF_3$ | diallylamino |
| 0 | $NHSO_2CF_3$ | di(n-propyl)amino |
| 0 | $NHSO_2CF_3$ | 3-pyrrolin-1-yl |
| 0 | $NHSO_2CF_3$ | pyrrolidin-1-yl |
| 0 | $NHSO_2CF_3$ | pyrrol-1-yl |
| 0 | $NHSO_2CF_3$ | n-propylamino |
| 0 | $NHSO_2CF_3$ | allylamino |
| 0 | $NHSO_2CF_3$ | 3-methylbut-2-enylamino |
| 0 | $NHSO_2CF_3$ | 3-methylbutylamino |
| 0 | $NHSO_2CF_3$ | 4,4,4-trifluorobutylamino |
| 0 | $NHSO_2CF_3$ | but-2-enylamino |
| 0 | H | 4,4-di-F-piperidin-1-yl |
| 0 | H | 4-$CF_3$-piperidin-1-yl |
| 0 | $NHSO_2$-(2-thienyl) | 4-$CF_3$-piperidin-1-yl |
| 1 | CN | 4,4-di-F-piperidin-1-yl |
| 0 | $NHSO_2CF_3$ | 4-F-piperidin-1-yl |
| 1 | $CONH_2$ | 4,4-di-F-piperidin-1-yl |
| 1 | $CONHCH_2CH_2CF_3$ | 4,4-di-F-piperidin-1-yl |
| 1 | $CONHCH_2CH_2F$ | 4,4-di-F-piperidin-1-yl |
| 0 | $NHSO_2CF_3$ | 3,3,3-trifluoropropylamino |

The compounds of formula I have an activity as inhibitors of the processing of APP by γ-secretase.

The invention also provides pharmaceutical compositions comprising one or more compounds of formula I or the pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 250 mg, for example 1, 2, 5, 10, 25, 50, 100, 200 or 250 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

The present invention further provides a method of treatment of a subject suffering from or prone to a condition associated with the deposition of β-amyloid which comprises administering to that subject an effective amount of a compound according to formula I or a pharmaceutically acceptable salt thereof. Preferably the condition is a neurological disease having associated β-amyloid deposition such as Alzheimer's disease.

For treating or preventing Alzheimer's Disease, a suitable dosage level is about 0.01 to 250 mg/Kg per day, preferably about 0.10 to 100 mg/Kg per day, especially about 1.0 to 50 mg/Kg, and for example about 10 to 30 mg/Kg of body weight per day. Thus, a dose of about 500 mg per person per day may be considered. The compounds may be administered on a regimen of 1 to 4 times per day. In some cases, however, dosage outside these limits may be used.

Compounds of formula I in which X represents CN, $N_3$, $OR^1$, $N(R^2)_2$, SCN, $SR^1$ or $SO_2R^1$ may be prepared by reaction of, respectively, MCN, $MN_3$, $MOR^1$, $HN(R^2)_2$, MSCN, $MSR^1$ or $MSO_2R^1$ with a compound of formula (1):

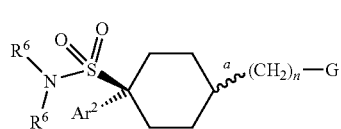

(1)

where M is a metal cation (preferably an alkali metal cation, such as Li or Na), G is a leaving group, $R^1$, $R^6$, $Ar^2$, and n have the same meanings as before, and bond a is cis with respect to $(R^6)_2NSO_2$ when n is 1, 2 or 3 and trans when n is 0. Suitable identities for G include halide (especially bromide or iodide) and alkyl- or arylsulphonate. Iodide and mesylate are particularly suitable. The metallated derivatives $MOR^{11}$, $MSR^1$ and $MSO_2R^1$ may be generated by reaction of the corresponding hydrides with NaOH, LiOH, NaH, BuLi, LiN($^i$Pr)$_2$ or similar, and are typically reacted in situ with the compounds (1).

Compounds of formula I in which X represents $S(O)R^1$ may be prepared from the corresponding compounds in which X represents $SR^1$ by oxidation with one equivalent of m-chloroperoxybenzoic acid. The oxidation takes place at ambient temperature in a dichloromethane-water mixture. Oxidation of the same compounds with two equivalents of m-chloroperoxybenzoic acid, or with sodium periodate in the presence of $RuO_2$ catalyst, provides an alternative route to compounds in which X represents $SO_2R^1$.

Compounds of formula I in which X represents $SO_2N(R^2)_2$ may be prepared by reaction of $(R^2)_2NH$ with a sulphonyl chloride of formula (2):

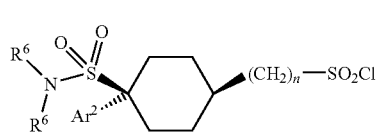

(2)

where $R^2$, $R^6$, $Ar^2$ and n have the same meanings as before. The reaction is typically carried out in dichloromethane at ambient temperature, either using excess of the amine or using an additional base such as potassium carbonate, pyridine or triethylamine.

Compounds of formula I in which X represents $OSO_2N(R^2)_2$ may be prepared by reaction of a sulphamoyl chloride $(R^2)_2NSO_2Cl$ with an alcohol of formula (3):

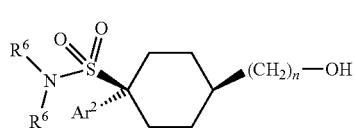

(3)

where $R^2$, $R^6$, $Ar^2$ and n have the same meanings as before. The reaction is typically carried out in dichloromethane at ambient temperature in the presence of a base such as pyridine or triethylamine. The sulphamoyl chlorides $(R^2)_2NSO_2Cl$ are available by reaction of $(R^2)^2NE$ with sulphuryl chloride in acetonitrile at ambient temperature.

Compounds of formula I in which X represents $NHCOR^1$, $NHCO_2R^1$, $NHSO_2R^1$ or $NHSO_2N(R^2)_2$ may be prepared by reacting an amine of formula (4) with, respectively, $R^1COCl$, $R^1OCOCl$, $R^1SO_2Cl$ and $(R^2)_2NSO_2Cl$:

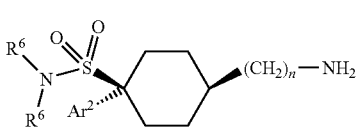

(4)

where $R^1$, $R^6$, $Ar^2$ and n have the same meanings as before. The reaction is typically carried out in dichloromethane at ambient or reduced temperature, in the presence of a base such as pyridine or triethylamine. Alternatively, the compounds in which X represents $NHCOR^1$ may be prepared by coupling of amines (4) with $R^1CO_2H$. Any of the standard peptide coupling procedures may be used, for example the use of 1-hydroxybenzotriazole or dimethylaminopyridine and 1-(3-dimethylaminopropyl)-3-ethylcarbodiimide.

An alternative route to the compounds of formula I in which X represents $NHSO_2N(R^2)_2$ involves reacting an amine of formula (4) with catechol sulphate and reacting the resulting sulphamate with $(R^2)_2NH$. The first step is typically carried out in THF at 0° C., and the second step at 80° C. in dioxan.

Compounds of formula I in which X represents NHCON$(R^2)_2$ may be prepared by treating a carboxylic acid of formula (5) first with diphenylphosphoryl azide, and then with $(R^2)_2NH$:

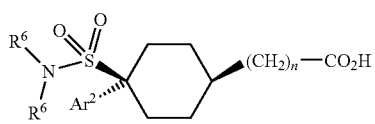
(5)

where $R^2$, $R^6$, $Ar^2$ and n have the same meanings as before. The first step is typically carried out in toluene at 110° C. in the presence of triethylamine, and the second step at ambient temperature in the same solvent.

Compounds of formula I in which X represents $COR^1$ may be prepared by reaction of a compound of formula (6a) with $R^1-M^1$:

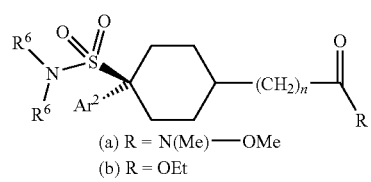
(6)
(a) R = N(Me)—OMe
(b) R = OEt where $M^1$ represents Li or MgBr and $R^6$, $Ar^2$ and n have the same meanings as before. The reaction is typically carried out in THF or diethyl ether at reduced temperature. When $M^1$ is MgBr, $R^1$ preferably represents substituted phenyl.

The compounds of formulae (3), (4), (5) and (6b) are themselves compounds in accordance with the invention.

The compounds of formula (1) in which G is iodide may be obtained by reaction of the corresponding compounds of formula (5) with iodosobenzene diacetate and iodine under irradiation. The compounds of formula (1) in which G is alkyl- or arylsulphonate are available from the reaction of the corresponding compounds of formula (3) (or, when n is zero, the trans isomers thereof) with the appropriate sulphonyl chloride.

The sulphonyl chlorides of formula (2) may be obtained by reaction of the compounds of formula (1) with potassium thioacetate, hydrolysis of the resulting thioester to give the corresponding thiol, then treatment of the thiol with potassium nitrate and sulphuryl chloride.

The alcohols of formula (3) in which n is 1, 2 or 3 are available by reduction of the acids of formula (5), the value of n increasing by 1 in the process. The alcohols of formula (3) in which n is 0 are available from the reduction of the cyclohexanones of formula (7).

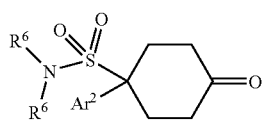
(7)

where $R^6$ and $Ar^2$ have the same meanings as before. Reduction with L-Selectride™ provides the cis isomer selectively. Reduction with sodium borohydride provides a mixture of cis and trans isomers which may be separated by chromatography.

The amines of formula (4) are available from the carboxylic acids (5) by sequential reaction with oxalyl chloride, sodium azide and benzyl alcohol, followed by hydrolysis of the resulting carbamate. Alternatively, they may be obtained from the mesylates of the alcohols (3) (or, when n is zero, the trans isomers thereof) by displacement with azide ion, followed by reduction.

The carboxylic acids of formula (5) in which n is 0 are available from the trans isomers of the alcohols (3) in which n is 0 by formation of the mesylate ester, followed by nucleophilic displacement with cyanide ion and hydrolysis of the resulting nitrile. The corresponding acids in which n is 1 are formed by condensation of cyclohexanones (7) with ethyl (diethoxyphosphinyl)acetate, followed by reduction of the resulting alkenyl ester (i.e. (6b)) and hydrolysis of the ester group. The corresponding acids in which n is 2 or 3 are obtainable by standard methods of homologation. For example, reduction of an acid (5) in which n is 1 provides an alcohol (3) in which n is 2, and mesylation, displacement with cyanide, and hydrolysis provides the corresponding acid in which n is 2. Repeating this process provides the acid (5) in which n is 3.

The N-methoxyamides (6a) are obtained from the corresponding carboxylic acids by treatment first with oxalyl chloride and then with N,O-dimethylhydroxylamine.

Cyclohexanones (7) are available from the alkylation of $Ar^2CH_2SO_2N(R^6)_2$ (8) with bis(iodides) (9), followed by hydrolysis of the ketal group:

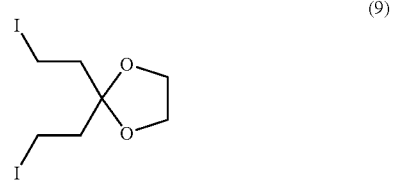
(9)

where $R^6$ and $Ar^2$ have the same meanings as before. The alkylation takes place in DMF in the presence of sodium hydride, and the hydrolysis may be carried out in aqueous acetic acid in the presence of p-toluenesulphonic acid.

The sulphonamides (8) are availble from the reaction of sulphonyl chlorides $Ar^2CH_2SO_2Cl$ (10) with $(R^6)_2NH$, where $R^6$ and $Ar^2$ have the same meanings as before. The reaction takes place in an inert solvent such as dichloromethane in the presence of a base such as triethylamine.

It will be apparent to those skilled in the art that individual compounds of formula I prepared by the above routes may be converted into other compounds in accordance with formula I by means of well known synthetic techniques such as alkylation, esterification, amide coupling, hydrolysis, oxidation and reduction. Such techniques may likewise be carried out on precursors of the compounds of formula I. For example, a compound of formula I in which X is SCN may be treated with trimethyl(trifluoromethyl)silane and tetrabutylammonium fluoride to provide the corresponding compound in which X is $SCF_3$, which in turn may be oxidised to the corresponding compound wherein X is $SO_2CF_3$.

Also, substituents on the aromatic group $Ar^2$ may be added or interconverted by means of standard synthetic processes carried out on the compounds of formula I or their precursors. For example, in esters (6b) a chlorine or bromine atom on $Ar^2$ may be replaced by vinyl by treatment with vinyltributyltin in the presence of tri-t-butylphosphine, cesium fluoride and tris (dibenzylideneacetone)dipalladium(0). Ozonolysis of the vinyl group provides the corresponding formyl derivative, which may be transformed in a variety of ways, including oxidation to the corresponding acid, reduction to the corresponding benzyl alcohol, and conversion to the corresponding nitrile by treatment with hydroxylamine then triphenylphosphine and carbon tetrachloride.

Similarly, the $R^6$ groups in compounds of formula I may be interconverted using standard techniques. For example, alkenyl groups represented by $R^6$ may be hydrogenated to provide the corresponding alkyl derivatives. Allyl groups represented by $R^6$ may be replaced with H by treatment with zirconocene dichloride or with diisobutylaluminium hydride and $NiCl_2$. Alternatively, compounds in which both $R^6$ groups are allyl may be converted to the corresponding 3-pyrrolin-1-yl derivatives by treatment with Grubbs catalyst, and then to the corresponding pyrrolidin-1-yl derivatives by hydrogenation or to the pyrrol-1-yl derivatives by oxidation. Compounds in which one or both $R^6$ groups represent H may be alkylated in conventional manner. Detailed procedures for such transformations are provided in the Examples section.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50-70% confluency. 10 mM sodium butyrate is added 4 hours prior to plating.

2) Cells are plated in 96-well plates at 35,000 cells/well/100 μL in Dulbecco's minimal essential medium (DMEM) (phenol red-free)+10% foetal bovine serum (FBS), 50 mM HEPES buffer (pH7.3), 1% glutamine.

3) Make dilutions of the compound plate. Dilute stock solution 18.2× to 5.5% DMSO and 11× final compound concentration. Mix compounds vigorously and store at 4° C. until use.

4) Add 10 μL compound/well, gently mix and leave for 18 h at 37° C., 5% $CO_2$.

5) Prepare reagents necessary to determine amyloid peptide levels, for example by Homogeneous Time Resolved Fluorescence (HTRF) assay.

6) Plate 160 μL aliquots of HTRF reagent mixture to each well of a black 96-well HTRF plate.

7) Transfer 40 μL conditioned supernatant from cell plate to HTRF plate. Mix and store at 4° C. for 18 hours.

8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.

9) Add 10 μL/well MTS/PES solution to the cells; mix and leave at 37° C.

10) Read plate when the absorbance values are approximately 0.4-0.8. (Mix briefly before reading to disperse the reduced formazan product).

11) Quantitate amyloid beta 40 peptide using an HTRF plate reader.

Alternative assays are described in *Biochemistry*, 2000, 39(30), 8698-8704. See also, *J. Neuroscience Methods*, 2000, 102, 61-68.

The Examples of the present invention all had an $ED_{50}$ of less than 1 μM, typically less than 0.5 μM, in most cases less than 100 nM, and in preferred cases less than 10 nM, in at least one of the above assays.

The following examples illustrate the present invention.

EXAMPLES

Example 1

N-[cis-4-(2,5-difluorophenyl)-4-(4-fluoropiperidine-1-sulfonyl)cyclohexyl]-1,1,1-trifluoromethane-sulfonamide

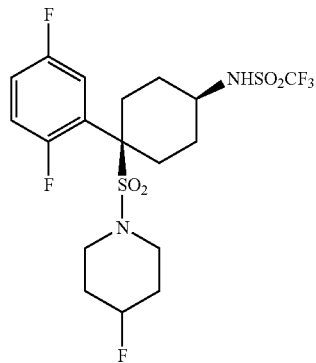

Step 1 1-(2,5-difluorophenylmethanesulfonyl)-4-fluoropiperidine

4-Fluoropiperidine.HBr (5 g, 27.3 mmol) in dichloromethane (50 ml) was cooled to 0° C. and treated with triethylamine (3.8 ml, 68.3 mmol), then 2,5-difluorophenyl-methane sulfonyl chloride (6.2 g, 27.3 mmol) in dichloromethane (50 ml) was added dropwise. The reaction mixture was left to stir at room temperature overnight, then quenched (0.1 N citric acid) and extracted (ethyl acetate). The organic phase was washed (brine), dried (magnesium sulfate) and evaporated in vacuo. The crude product was chromatographed on silica, eluting with 20-30% ethyl acetate/isohexane to give the title product. (3.87 g, 48%).

$^1$H NMR (500 MHz, CDCl$_3$) δ 1.75-1.90 (4H, m), 3.15-3.22 (2H, m), 3.30-3.36 (2H), m), 4.24 (2H, s), 4.73-4.76 (0.5H, m), 4.85-4.88 (0.5H, m), 7.03-7.12 (2H, m), 7.22-7.25 (1H, m).

Step 2 1-[8-(2,5-difluorophenyl)-1,4-dioxa-spiro[4,5]decane-8-sulfonyl]-4-fluoropiperidine

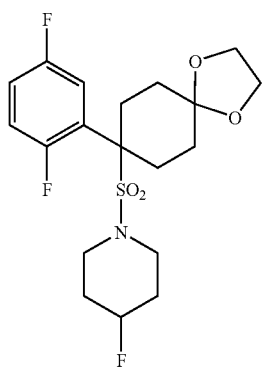

To the product of Step 1 (3.87 g, 13.2 mmol) in dimethylformamide (50 ml) at room temperature was added 2,2-bis(2-iodoethyl)-[1,3]-dioxolane (5.55 g, 14.5 mmol) followed (portionwise) by sodium hydride (1.16 g, 60% w/w in mineral oil, 29.1 mmol). After stirring at room temperature overnight the mixture was quenched (water) and extracted (ethyl acetate). The organic phase was washed (water, brine), dried (magnesium sulfate) and evaporated in vacuo. The crude material was chromatographed on silica, eluting with 10-20% ethyl acetate/isohexane to give the title compound (2.99 g, 54%).

$^1$H NMR (500 MHz, CDCl$_3$) δ 1.47 (2H, td, J=3.4 and 13.9 Hz), 1.70-1.85 (6H, m), 2.38 (2H, t, J=13.7 Hz), 2.77 (2H, bs), 2.96-3.38 (4H, vbs), 3.89-3.91 (2H, m), 3.94-3.97 (2H, m), 4.71-4.90 (1H, m), 7.05-7.08 (2H, m), 7.23-7.25 (1H, m).

Step 3 4-(2,5-difluorophenyl)-4-(4-fluoropiperidine-1-sulfonyl)-cyclohexanone

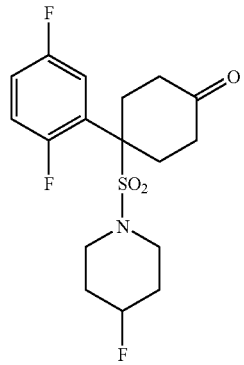

The product of Step 2 (2.99 g, 7.14 mmol) and p-toluenesulfonic acid (1.62 g, 8.56 mmol) in acetic acid/water (40 ml/10 ml) were heated at 50° C. for 3 hours and then diluted (water) and extracted (diethyl ether). The organic phase was washed (saturated sodium hydrogen carbonate, brine), dried (magnesium sulfate) and evaporated in vacuo. The crude product was azeotroped with toluene, followed by ethyl acetate, followed by dichloromethane. The crude product then was chromatographed on silica, eluting with 30% ethyl acetate/isohexane to give the cyclohexanone (1.7 g, 64%).

$^1$H NMR (500 MHz, CDCl$_3$) δ 1.71-1.89 (4H, m), 2.19-2.28 (2H, m), 2.47-2.55 (4H, m), 3.04-3.40 (6H, m), 4.75-4.95 (1H, m), 7.14-7.17 (2H, m), 7.31-7.36 (1H, m).

Step 4 trans-4-(2,5-difluorophenyl)-4-(4-fluoropiperidine-1-sulfonyl)-cyclohexanol

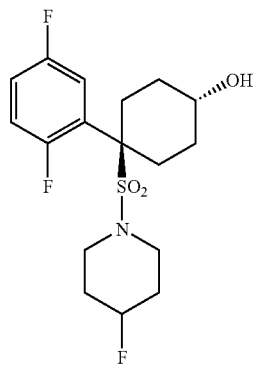

The cyclohexanone (1.7 g, 4.53 mmol) in ethanol/tetrahydrofuran (30 ml/5 ml) was cooled to −78° C. Sodium borohydride (0.34 g, 9.07 mmol) was added portionwise. After stirring for 2 hours at −78° C., the mixture was quenched at −78° C. (0.1 N citric acid), allowed to warm to room temperature and extracted (ethyl acetate). The organic phase was washed (water, brine), dried (magnesium sulfate) and evaporated in vacuo to give the crude alcohol (1.56 g, 91%).

$^1$H NMR (500 MHz, CDCl$_3$) δ 1.19-1.27 (2H, m), 1.43-1.64 (2H, m), 1.70-1.85 (4H, m), 1.97-2.03 (1H, m), 2.12 (2H, t, J=13.8 Hz), 2.65-3.33 (6H, m), 3.73-3.78 (1H, m), 4.71-4.89 (1H, m), 7.06-7.10 (2H, m), 7.23-7.27 (1H, m).

Step 5 cis-4-(2,5-difluorophenyl)-4-(4-fluoropiperidine-1-sulfonyl)-cyclohexylamine

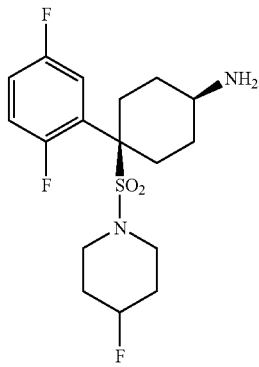

The alcohol (1.56 g, 4.14 mmol) in dichloromethane (30 ml) at −10° C. was treated with triethylamine (0.98 ml, 7.03 mmol), followed by methanesulfonyl chloride (0.48 ml, 6.21 mmol). The mixture was stirred at room temperature for 1.5 hours then diluted (dichloromethane) Extractive work-up afforded the crude mesylate. (1.80 g, 96%). Sodium azide (0.39 g, 5.93 mmol) was added to a solution of the mesylate (1.80 g, 3.96 mmol) in N,N-dimethylformamide (40 ml) and heated at 95° C. for 2 hours. Further sodium azide (0.13 g, 1.99 mmol) was added and the mixture was stirred for 4 hours, then quenched (water) and extracted (ethyl acetate). The organic phase was washed (water, brine), dried (magnesium sulfate) and evaporated in vacuo to give crude azide (1.37 g, 86%).

The azide (1.37 g, 3.41 mmol) and triphenylphosphine (1.79 g, 6.82 mmol) in tetrahydrofuran/water (30 ml/3 ml) were refluxed overnight, then quenched (water) and extracted (ethyl acetate/isohexane). The organic phase was washed (water, brine), dried (magnesium sulfate) and evaporated in vacuo. The crude product was chromatographed on silica, eluting with 5% ammonia in methanol (2.0 N)/dichloromethane to give the title amine. (0.76 g, 59%).

$^1$H NMR (400 MHz, CDCl$_3$) δ 1.38 (2H, s), 1.51-1.58 (2H, m), 1.61-1.70 (2H, m), 1.75-1.88 (4H, m), 2.46-2.57 (4H, m), 2.68-3.30 (5H, m), 4.70-4.91 (1H, m), 7.04-7.08 (2H, m), 7.23-7.28 (1H, m).

Step 6 N-[cis-4-(2,5-difluorophenyl)-4-(4-fluoropiperidine-1-sulfonyl)cyclohexyl]-1,1,1-trifluoromethanesulfonamide The amine (0.20 g, 0.53 mmol) in dichloromethane (15 ml) was treated with triethylamine (0.07 ml, 0.53 mmol), cooled to −78° C. and trifluoromethanesulfonic anhydride (0.18 ml, 1.06 ml) was added dropwise. The mixture was stirred for 3 hours at −78° C. then quenched (0.1 N citric acid) and extracted (dichloromethane). The organic phase was washed (water, brine), dried (magnesium sulfate) and evaporated in vacuo. The crude product was chromatographed on silica, eluting with 20% ethyl acetate/isohexane to give the title compound (0.17 g, 64%).

$^1$H NMR (400 MHz, CDCl$_3$) δ 1.63-170 (2H, s), 1.71-190 (4H, m), 1.95-2.03 (2H, m), 2.37 (2H, t, J=13.0 Hz), 2.61-2.73 (2H, m), 2.85-3.34 (4H, m), 3.77-3.80 (1H, m), 4.68-4.92 (1H, m), 5.72 (1H, d, J=8.2 Hz), 7.09-7.12 (2H, m), 7.21-7.25 (1H, m).

Example 2

N-[cis-4-(2,5-difluorophenyl)-4-(4-trifluoromethylpiperidne-1-sulfonyl)-cyclohexyl]-1,1,1-trifluoromethanesulfonamide

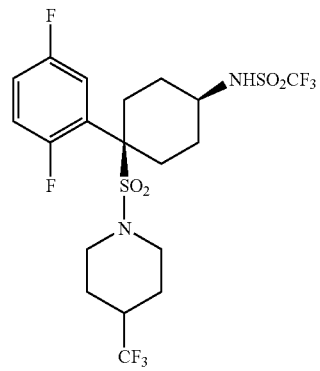

Prepared as described in Example 1, substituting 4-trifluoromethylpiperidine for 4-fluoropiperidine in Step 1.

$^1$H NMR (500 MHz, CDCl$_3$) δ 1.45-1.58 (2H, bs), 1.61-1.70 (2H, m), 1.74-1.77 (2H, m), 1.99-2.02 (2H, m), 2.04-2.13 (1H, bs), 2.38 (2H, t, J=13.3 Hz), 2.57-2.75 (4H, bs), 3.28-3.65 (2H, vbs), 3.75-3.82 (1H, m), 5.65-5.72 (1H, bs), 7.08-7.12 (2H, m), 7.22-7.24 (2H, m).

Example 3

N-[cis-4-(2,5-difluorophenyl)-4-(4,4-difluoropiperidine-1-sulfonyl)cyclohexyl]-1,1,1-trifluoromethanesulfonamide

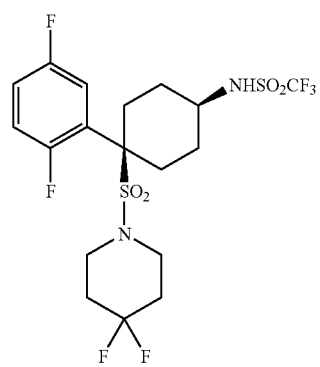

Prepared as described in Example 1, substituting 4,4-difluoropiperidine for 4-fluoropiperidine in Step 1.

Example 4

Thiophene-2-sulfonic acid cis-[4-(2,5-difluorophenyl)-4-(4-trifluoromethyl-piperidine-1-sulfonyl)cyclohexyl]-amide

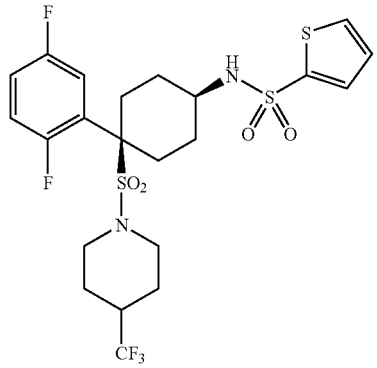

Prepared as for Example 2, carrying out the final step at ambient temperature using thiophene-2-sulfonyl chloride in place of trifluoromethanesulfonic anhydride.

$^1$H NMR (400 MHz, CDCl$_3$) δ 1.44-1.53 (4H, m), 1.73-1.84 (4H, m), 2.05-2.14 (1H, m), 2.29 (2H, t, J=13.4 Hz), 2.53-2.75 (4H, m), 3.46-3.54 (3H, m), 5.00 (1H, d, J=6.6 Hz), 7.03-7.09 (3H, m), 7.17-7.21 (1H, m), 7.58-7.62 (2H, m).

Example 5 cis-N,N-diallyl-1-(2,5-difluorophenyl)-4-{[(trifluoromethyl)sulfonyl]amino}cyclohexanesulfonamide

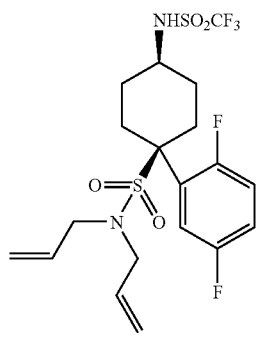

Prepared by the procedure of Example 1, using diallylamine in Step 1.

$^1$H NMR (500 MHz, CDCl$_3$) 7.26-7.22 (1H, m), 7.11-7.08 (2H, m), 6.05 (1H, brs), 5.65-5.62 (2H, m), 5.19-5.08 (4H, m), 3.79 (1H, brm), 3.48 (4H, brs), 2.75 (2H, vbrs), 2.38 (2H, appt), 2.05-1.98 (2H, m), 1.68-1.62 (2H, m).

Example 6 cis-1-(2,5-difluorophenyl)-N,N-dipropyl-4-{[(trifluoromethyl)sulfonyl]amino}cyclohexanesulfonamide

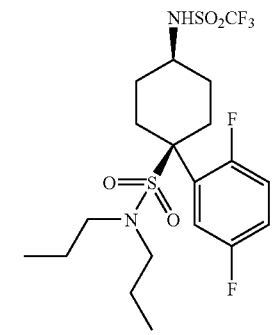

A solution of the product of Example 5 (70 mg) and 5% Pd—C (30 mg) in ethyl acetate (5 ml) was hydrogenated at 50 psi for 2 h. The catalyst was removed by filtration and the organic solvent was removed by evaporation under reduced pressure to give the title compound (65 mg, 100%) as a white solid.

Example 7

N-[cis-4-(2,5-difluorophenyl)-4-(2,5-dihydro-1H-pyrrol-1-ylsulfonyl)cyclohexyl]-1,1,1-trifluoromethanesulfonamide

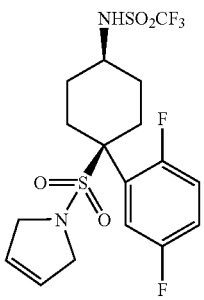

A solution of the product of Example 5 (320 mg) in dichloromethane (70 ml) was treated with 1,3-bis-(2,4,6-trimethylphenyl)-2-imidazolidinylidene)dichloro(phenylmethylene)-(tricyclohexylphosphine)ruthenium (5 mg) and stirred at room temperature overnight. The reaction mixture was evaporated in vacuo and purified by flash column chromatography to give the title product (300 mg, 99%) as a white solid.

$^1$H NMR (500 MHz, CDCl$_3$) 7.27-7.23 (1H, m), 7.11-7.04 (2H, m), 5.83 (1H, s), 5.64 (2H, s), 3.91 (4H, vbrs), 3.79 (1H, brs), 2.72 (2H, appd), 2.44 (2H, appt), 2.02-1.99 (2H, m), 1.72-1.65 (2H, m).

Example 8

N-[cis-4-(2,5-difluorophenyl)-4-(pyrrolidin-1-ylsulfonyl)cyclohexyl]-1,1,1-trifluoromethanesulfonamide

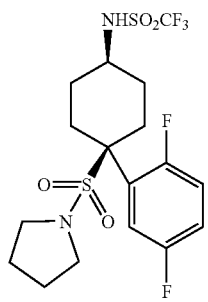

The product of Example 7 (65 mg) and 5% Pd—C (30 mg) in ethyl acetate (5 ml) was hydrogenated at 50 psi for 2 h. The catalyst was removed by filtration and the organic solvent was removed by evaporation under reduced pressure to give the title compound (65 mg, 100%) as a white solid. $^1$H NMR (500 MHz, CDCl$_3$) 7.26-7.23 (1H, m), 7.11-7.04 (2H, m), 6.30 (1H, d, J=8.2), 3.79-3.77 (1H, m), 3.07 (4H, vbrs), 2.72 (2H, appd), 2.45 (2H, appt), 2.05-1.98 (2H, m), 1.80-1.63 (6H, m).

Example 9

N-[cis-4-(2,5-difluorophenyl)-4-(1H-pyrrol-1-ylsulfonyl)cyclohexyl]-1,1,1-trifluoromethanesulfonamide

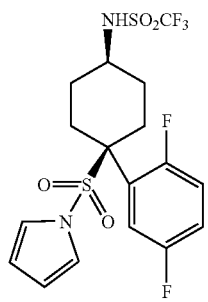

A suspension of the product of Example 7 (50 mg) and manganese dioxide (100 mg) in benzene (5 ml) was refluxed for 6 h. The reaction mixture was cooled and filtered. The filtrate was evaporated in vacuo. Purification by column chromatography gave the title compound (26 mg, 52%) as a white solid. $^1$H NMR (500 MHz, CDCl$_3$) 7.11-7.07 (1H, m), 7.02-6.96 (1H, m), 6.87-6.83 (1H, m), 6.60 (2H, brs), 6.22 (2H, brs), 5.95 (1H, brs), 3.80 (1H, brs), 2.70 (2H, brs), 2.47 (2H, appt), 2.06-2.04 (2H, m), 1.68-1.63 (2H, m).

Example 10 cis-1-(2,5-difluorophenyl)-N-propyl-4-{[(trifluoromethyl)sulfonyl]amino}cyclohexanesulfonamide

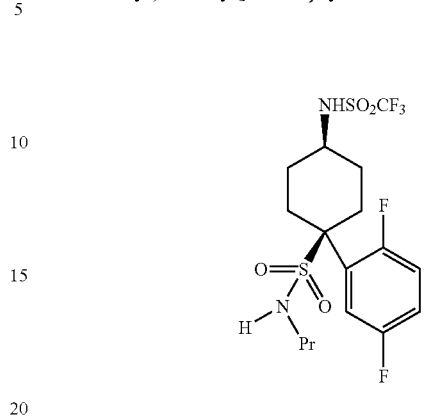

A solution of the product of Example 5 (320 mg) in toluene (10 ml) was treated at room temperature with NiCl$_2$(dppp) (140 mg) and DIBAL-H (8 equivalents) and stirred at room temperature for 2 h. The reaction mixture was quenched with water, extracted with ethyl acetate and purified by column chromatography to give the title compound (55 mg, 18%) as a white solid. $^{19}$F NMR (470 MHz, CDCl$_3$) −78, −113, −118.

Example 11 cis-N-allyl-1-(2,5-difluorophenyl)-4-{[(trifluoromethyl)sulfonyl]amino}cyclohexanesulfonamide

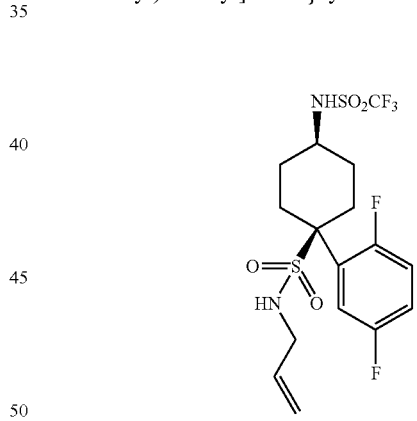

A solution of the product of Example 5 (250 mg) and zirconocene dichloride (150 mg) in THF (5 ml) was cooled to −78° C. and treated with butyllithium (3 equivalents). The reaction mixture was stirred for 10 minutes, then warmed to room temperature and stirred for 2 h. The reaction mixture was cooled to −78° C. and treated with 2N aqueous HCl. The reaction mixture was warmed to room temperature and diluted with ethyl acetate. The organic layer was separated, washed with NaHCO$_3$ solution and brine, dried (MgSO$_4$), filtered and evaporated in vacuo. Purification by column chromatography gave the title compound (65 mg, 28%) as a white solid. ($^{19}$F NMR (470 MHz, CDCl$_3$) −78, −113, −117) and also the bis(de-allylated) byproduct as a white solid.

Example 12 cis-1-(2,5-difluorophenyl)-N-(3-methylbut-2-en-1-yl)-4-{[(trifluoromethyl)sulfonyl]amino}cyclohexanesulfonamide

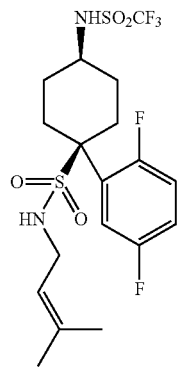

The product from Example 11 (20 mg) was dissolved in 2-methyl-2-butene (10 ml) and DCM (2 ml). 1,3-Bis-(2,4,6-trimethylphenyl)-2-imidazolidinylidene)dichloro(phenylmethylene)-(tricyclohexylphosphine)ruthenium (10 mg) was added and the reaction mixture was refluxed for 30 mins. The reaction mixture was filtered through silica, washing with ether. The filtrate was evaporated. Purification by flash column chromatography gave the title compound (10 mg). $^{19}$F NMR (470 MHz, CDCl$_3$) −78.2, −113, −117.6.

Example 13 cis-1-(2,5-difluorophenyl)-N-(3-methylbutyl)-4-{[(trifluoromethyl)sulfonyl]amino}cyclohexanesulfonamide

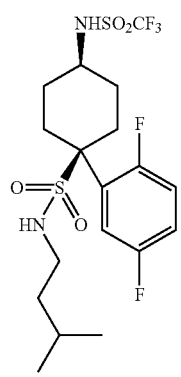

The product of Example 12 (5 mg) and 5% Pd—C (5 mg) in ethyl acetate (5 ml) was hydrogenated at 50 psi for 2 h. The catalyst was removed by filtration and the organic solvent was removed by evaporation under reduced pressure to give the title compound (5 mg, 100%) as a white solid. $^{19}$F NMR (470 MHz, CDCl$_3$) −78, −113.2, −117.5.

Example 14 cis-1-(2,5-difluorophenyl)-N-(4,4,4-trifluorobutyl)-4-{[(trifluoromethyl)sulfonyl]amino}cyclohexanesulfonamide

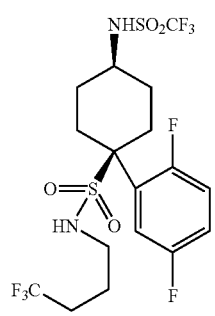

A solution of the byproduct from Example 11, Cs$_2$CO$_3$, 4,4,4-trifluorobutyl iodide and DMF was stirred at room temperature for 3 days. Aqueous work up gave the title compound as a white solid.

Example 15 cis-1-(2,5-difluorophenyl)-N-(2E-butenyl)-4-{[(trifluoromethyl)sulfonyl]amino}cyclohexanesulfonamide

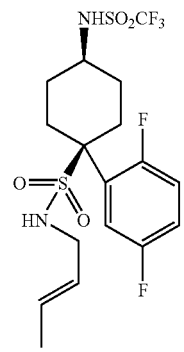

The product of Example 11 (20 mg) was dissolved in DCM (2 ml) in a sealed tube and treated with 2-trifluoromethyl propene (2 ml), containing about 3% of 2-propene. 1,3-Bis-(2,4,6-trimethylphenyl)-2-imidazolidinylidene)dichloro(phenylmethylene)-(tricyclohexylphosphine)ruthenium (2 mg) was added and the reaction mixture was stirred at room temperature for 72 h. The reaction mixture was filtered through silica, washing with ether. The filtrate was evaporated. Purification by flash column chromatography gave the title compound (10 mg).

What is claimed is:

1. A compound according to formula I:

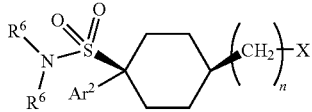

wherein n is 1 or 2;

X represents CN, $N_3$, OH, $CO_2H$, $CO_2R^1$, $CON(R^2)_2$, $SO_2R^1$, $SO_2N(R^2)_2$ or $OSO_2N(R^2)_2$;

$R^1$ represents $CF_3$, $C_{1-6}$alkyl, $C_{2-6}$alkenyl, $C_{3-9}$cycloalkyl or $C_{3-6}$cycloalkyl$C_{1-6}$alkyl, any of which optionally bear up to 2 substituents selected from halogen, CN, $CF_3$, $OR^3$, aryloxy, $COR^3$, $CO_2R^3$, $OCOR^4$, $SO_2R^4$, $N(R^5)_2$, and $CON(R^5)_2$, or $R^1$ represents aryl or aryl$C_{1-6}$alkyl;

each $R^2$ independently represents H or $C_{1-6}$alkyl, $C_{2-6}$alkenyl, $C_{3-9}$cycloalkyl or $C_{3-6}$cycloalkyl$C_{1-6}$alkyl, any of which optionally bear up to 2 substituents selected from halogen, CN, $CF_3$, $OR^3$, $COR^3$, $CO_2R^3$, $OCOR^4$, $SO_2R^4$ and $CON(R^5)_2$;

$R^3$ represents H or $C_{1-4}$alkyl;

$R^4$ represents $C_{1-4}$alkyl;

$R^5$ represents H or $C_{1-4}$alkyl;

the two $R^6$ groups and the nitrogen to which they are attached complete an N-heterocyclyl group that is six-membered which is attached through N, wherein the one nitrogen is the only heteroatom, or the two $R^6$ groups and the nitrogen to which they are attached complete an N-heterocyclyl group that is five-membered which is attached through N or a heteroaryl group that is five-membered consisting of carbon and nitrogen atoms which is attached through N;

$Ar^2$ represents phenyl which bears 0-3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

"aryl" at every occurrence thereof refers to phenyl or heteroaryl which optionally bear up to 3 substituents selected from halogen, CN, $NO_2$, $CF_3$, $OCF_3$, OH, $COR^3$, $CO_2R^3$, $OCOR^4$, $N(R^5)_2$, $CON(R^5)_2$ and optionally-substituted $C_{1-6}$alkyl, $C_{1-6}$alkoxy, $C_{2-6}$alkenyl or $C_{2-6}$alkenyloxy wherein the substituent on the optionally-substituted $C_{1-6}$alkyl, $C_{1-6}$alkoxy, $C_{2-6}$alkenyl or $C_{2-6}$alkenyloxy is selected from halogen, CN, $CF_3$, phenyl, $OR^3$, $CO_2R^3$, $OCOR^{3a}$, $N(R^5)_2$ and $CON(R^5)_2$; and "N-heterocyclyl" at every occurrence thereof refers to a heterocyclic ring system, said ring system being non-aromatic and consisting of the indicated number of atoms, and optionally bearing up to 3 substituents selected from oxo, halogen, CN, $NO_2$, $CF_3$, $OCF_3$, $OR^3$, $COR^3$, $CO_2R^3$, $OCOR^4$, $OSO_2R^4$, $N(R^5)_2$, $CON(R^5)_2$ and optionally-substituted phenyl, $C_{1-6}$alkyl, $C_{1-6}$alkoxy, $C_{2-6}$alkenyl or 6alkenyloxy wherein the substituent on the optionally-substituted phenyl, $C_{1-6}$alkyl, $C_{1-6}$alkoxy, $C_{2-6}$alkenyl or $C_{2-6}$alkenyloxy is selected from halogen, CN, $CF_3$, $OR^3$, $CO_2R^3$, $OCOR^4$, $N(R^5)_2$ and $CON(R^5)_2$;

or a pharmaceutically acceptable salt thereof.

2. A compound according to claim 1 wherein X represents $CO_2H$, $CO_2R^1$, $CON(R^2)_2$, $SO_2R^1$ or $SO_2N(R^2)_2$.

* * * * *